(12) United States Patent
Huh

(10) Patent No.: US 11,394,166 B2
(45) Date of Patent: Jul. 19, 2022

(54) LASER IRRADIATING DEVICE

(71) Applicant: Jin Huh, Yongin-si (KR)

(72) Inventor: Jin Huh, Yongin-si (KR)

(*) Notice: Subject to any disclaimer, the term of this patent is extended or adjusted under 35 U.S.C. 154(b) by 89 days.

(21) Appl. No.: 17/052,203

(22) PCT Filed: May 14, 2019

(86) PCT No.: PCT/KR2019/005773
§ 371 (c)(1),
(2) Date: Nov. 2, 2020

(87) PCT Pub. No.: WO2019/221480
PCT Pub. Date: Nov. 21, 2019

(65) Prior Publication Data
US 2021/0091528 A1  Mar. 25, 2021

(30) Foreign Application Priority Data
May 17, 2018  (KR) .................. 10-2018-0056473

(51) Int. Cl.
*H01S 3/091* (2006.01)
*H01S 3/06* (2006.01)
(Continued)

(52) U.S. Cl.
CPC ............ *H01S 3/0912* (2013.01); *H01S 3/061* (2013.01); *H01S 3/093* (2013.01); *H01S 3/1312* (2013.01);
(Continued)

(58) Field of Classification Search
CPC ......... H01S 3/092–0931; H01S 3/1022; H01S 3/1024; H01S 3/1312; H01S 3/091–0933
See application file for complete search history.

(56) References Cited

U.S. PATENT DOCUMENTS 3,806,829 A * 4/1974 Duston ............. B23K 26/0622
219/121.61
4,027,273 A * 5/1977 Yang ................... H01S 3/042
372/36
(Continued)

FOREIGN PATENT DOCUMENTS

CN  104248453 A * 12/2014 ........... A61B 5/0095
CN  104248453 B * 12/2016 ........... A61B 5/0095
(Continued)

OTHER PUBLICATIONS

International Search Report for PCT/KR2019/005773 dated Aug. 22, 2019 from Korean Intellectual Property Office.

*Primary Examiner* — Joshua King
(74) *Attorney, Agent, or Firm* — Revolution IP, PLLC

(57) ABSTRACT

A laser irradiating device preferably includes: a reflector having a receiving space formed therein; a flash lamp inserted and mounted in the reflector to generate light; a laser rod for resonating light incident from the flash lamp to emit a laser; a capacitor for storing, for a predetermined time interval, voltage to be supplied to the flash lamp; a digital variable resistor unit for outputting different voltages according to configured resistance values; a voltage increasing unit for increasing voltage input from the digital variable resistor unit and supplying the increased voltage to the capacitor; a control unit which stores resistance values corresponding to laser irradiating levels and configures a resistance value corresponding to the configured laser irradiating level; and a trigger circuit unit turned on according to a control of the user to supply a charge voltage of the capacitor to the flash lamp.

6 Claims, 4 Drawing Sheets

(51) Int. Cl.
*H01S 3/093* (2006.01)
*H01S 3/131* (2006.01)
*A61B 18/20* (2006.01)
*A61B 18/00* (2006.01)
*A61N 5/06* (2006.01)
*A61N 5/067* (2006.01)

(52) U.S. Cl.
CPC ... *A61B 18/203* (2013.01); *A61B 2018/00452* (2013.01); *A61N 5/067* (2021.08); *A61N 5/0616* (2013.01)

(56) References Cited

U.S. PATENT DOCUMENTS

| | | | | |
|---|---|---|---|---|
| 4,345,330 | A * | 8/1982 | Howie | H01S 3/134 372/38.07 |
| 4,644,550 | A * | 2/1987 | Csery | A61F 9/00823 372/5 |
| 4,829,530 | A * | 5/1989 | Sato | H01S 3/092 372/38.07 |
| 5,498,935 | A * | 3/1996 | McMahan | H01S 3/092 315/241 P |
| 5,692,004 | A * | 11/1997 | Greene | H01S 3/102 372/92 |
| 6,193,711 | B1 * | 2/2001 | Connors | A61B 18/203 372/25 |
| 6,355,905 | B1 * | 3/2002 | Sasaki | H01S 3/102 219/121.62 |
| 6,512,782 | B1 * | 1/2003 | Hsia | H01S 3/1022 372/25 |
| 7,097,639 | B1 * | 8/2006 | Almeida | A61B 18/203 607/91 |
| 7,630,420 | B2 * | 12/2009 | Boutoussov | H01S 3/0912 372/25 |
| 2003/0012234 | A1 * | 1/2003 | Watson | H01S 3/104 372/38.1 |
| 2003/0227953 | A1 * | 12/2003 | Hsia | H01S 3/1022 372/53 |
| 2005/0285015 | A1 | 12/2005 | Lee | |
| 2007/0071047 | A1 * | 3/2007 | Huang | H01S 3/097 372/55 |
| 2013/0308668 | A1 * | 11/2013 | Guskov | H01S 3/10 372/38.04 |
| 2014/0241387 | A1 * | 8/2014 | Ortiz | H05B 45/48 372/38.02 |
| 2015/0005612 | A1 * | 1/2015 | Suzuki | A61B 5/0095 600/407 |
| 2015/0045778 | A1 * | 2/2015 | Ichihara | H01S 3/1022 372/81 |

FOREIGN PATENT DOCUMENTS

| | | | | |
|---|---|---|---|---|
| DE | 102007024111 A1 * | 12/2008 | | H01S 3/1022 |
| EP | 0050058 A1 * | 4/1982 | | |
| EP | 0989640 A2 * | 3/2000 | | |
| JP | 06-314831 A | 11/1994 | | |
| KR | 20-2000-0014427 U | 7/2000 | | |
| KR | 10-0544204 B1 | 1/2006 | | |
| KR | 10-0551479 B1 | 2/2006 | | |
| KR | 101163124 B1 * | 7/2012 | | |
| KR | 10-2014-0128753 A | 11/2014 | | |

\* cited by examiner

[Figure 1]
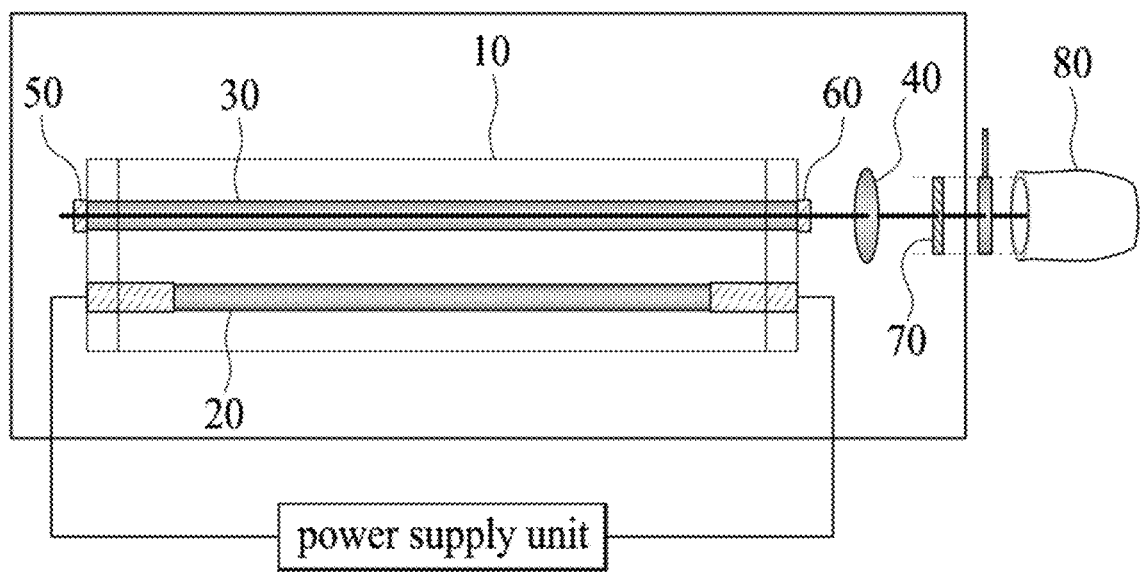

[Figure 2]
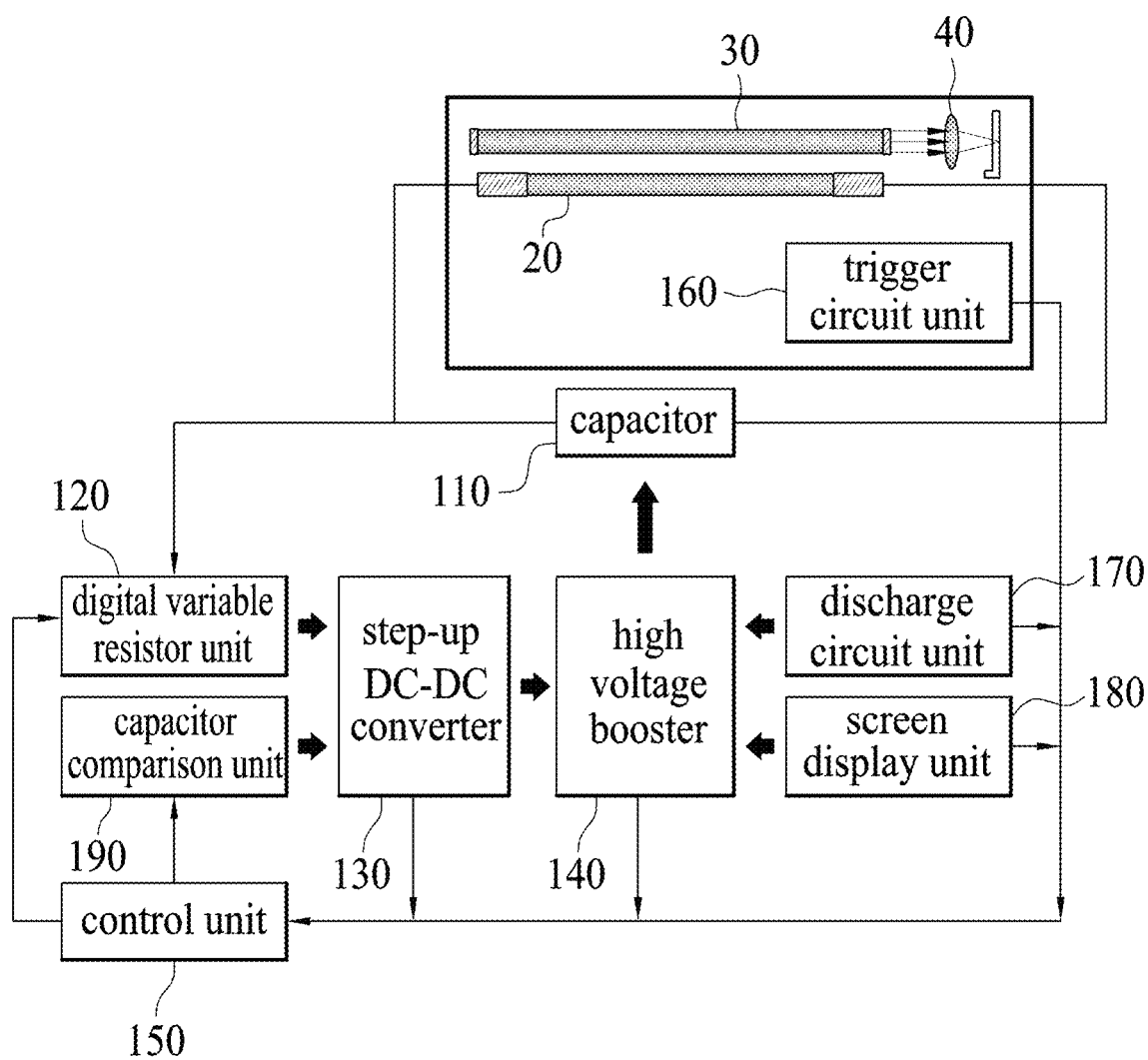

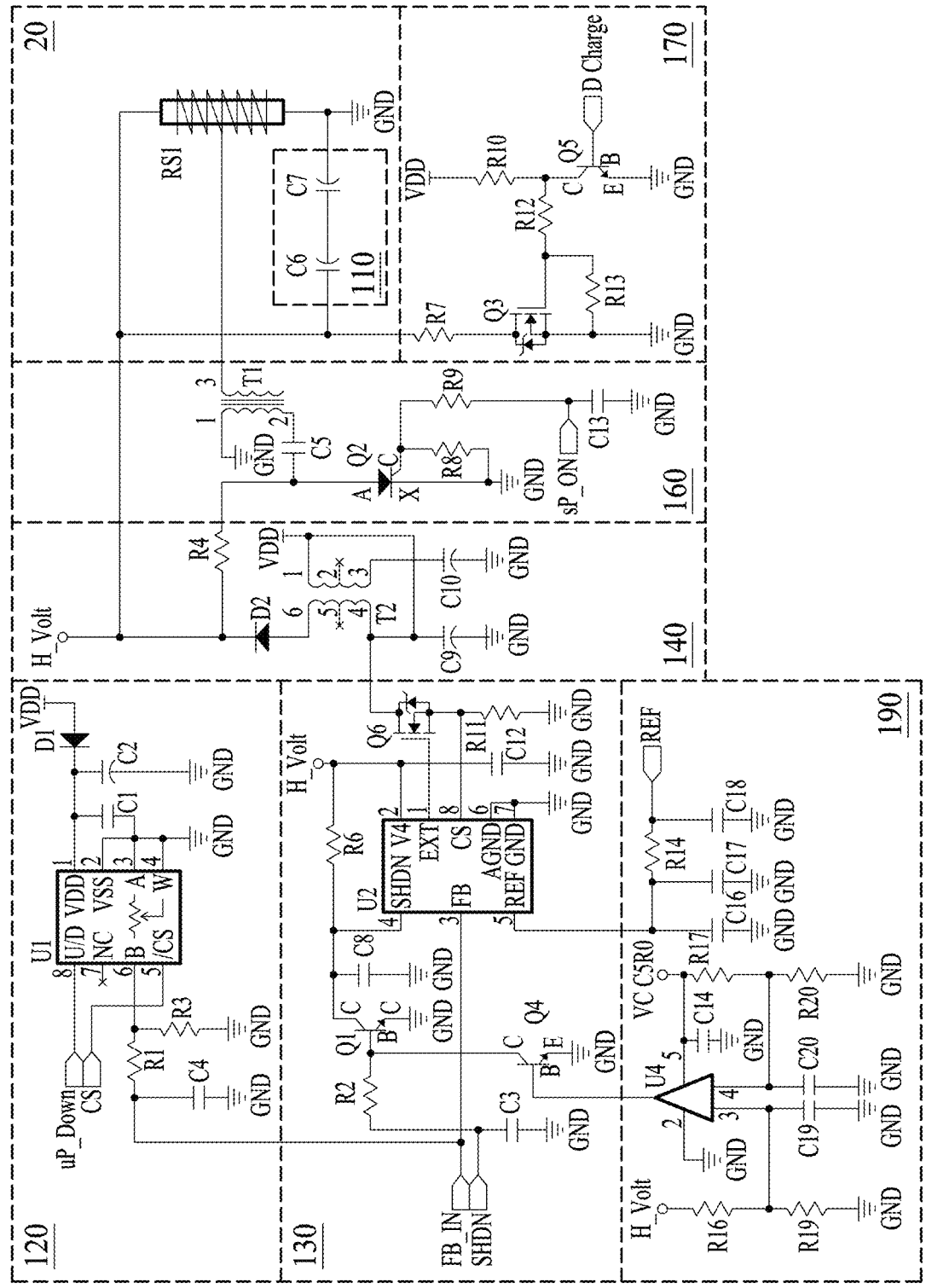
[Figure 3]

[Figure 4]
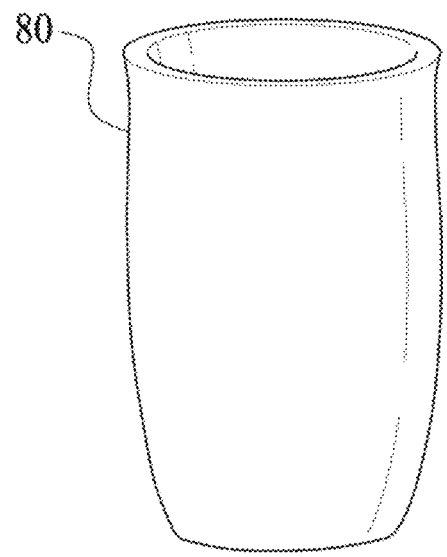
[Figure 5]
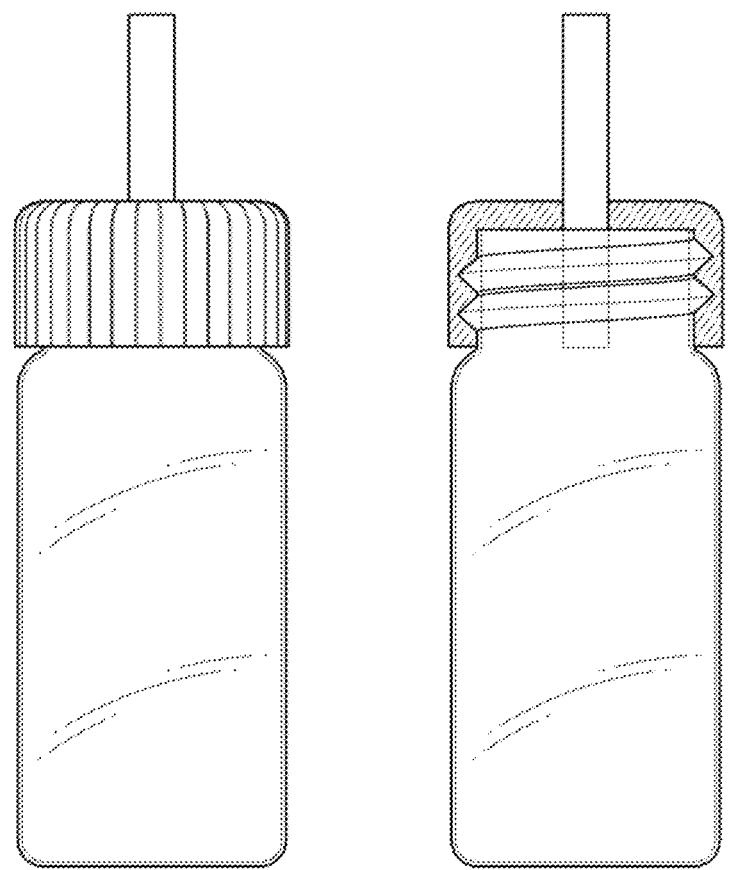

LASER IRRADIATING DEVICE

TECHNICAL FIELD

The present disclosure relates to a laser irradiating device. More particularly, the disclosure relates to a laser irradiating device intended to stably adjust a laser irradiation intensity.

BACKGROUND ART

A laser irradiating device for medical purposes is used to take blood, administer drugs, or remove moles or freckles from skin by irradiating laser beams onto the skin and thereby perforating the skin.

Such a laser irradiating device is gradually increasing in demand because it has less pain and can perform a medical procedure rapidly as compared with a conventional syringe for taking blood or administering drugs or a surgical instrument for removing moles or freckles.

Depending on whether the skin perforation using the laser is for taking blood, administering drugs, or removing moles or freckles, and since the thickness or nature of the skin varies depending on a patient's gender, age, or occupation, it is necessary to adjust the size or depth of a hole by changing the irradiation intensity of a laser beam.

However, a conventional laser irradiating device is fixed in laser irradiation intensity, and there are slight differences in irradiation intensity between manufacturers.

When the laser irradiation intensity is fixed, the laser irradiating device is problematic in that it is unsuitable for various purposes of laser perforation, it is impossible to make a hole having a desired size and depth according to a patient's gender, age, or occupation, or a larger hole may be made as compared with a desired size and depth, thus leaving scars on the skin.

Thus, a laser irradiating device capable of adjusting the laser irradiation intensity has been developed. However, the conventional laser irradiating device is problematic in that the noise of a circuit itself is severe, so that it is impossible to precisely adjust the intensity.

DISCLOSURE

Technical Problem

Accordingly, the present disclosure has been made keeping in mind the above problems occurring in the related art, and is intended to provide a laser irradiating device capable of adjusting the irradiation intensity of laser in stages by a user's manipulation.

Another object of the present disclosure is to provide a laser irradiating device, in which the generation of noise and the leakage of voltage are prevented by physically separating a trigger circuit unit, thus stably adjusting a laser irradiation intensity.

A further object of the present disclosure is to provide a laser irradiating device, in which a capacitor, a digital variable resistor, a voltage increasing unit, and a control unit are installed to be spaced apart from each other by a predetermined insulating distance, thus preventing the leakage of voltage and the generation of noise and thereby stably adjusting a laser irradiation intensity.

Technical Solution

In order to accomplish the above-described object, the present disclosure provides a laser irradiating device including a reflector having a receiving space formed therein; a flash lamp inserted and mounted in the reflector to generate light; a laser rod for resonating light incident from the flash lamp to emit a laser; a capacitor for storing, for a predetermined time, voltage to be supplied to the flash lamp; a digital variable resistor unit for outputting different voltages according to set resistance values; a voltage increasing unit for increasing voltage input from the digital variable resistor unit and supplying the increased voltage to the capacitor; a control unit storing resistance values corresponding to laser irradiating levels and setting a resistance value of the digital variable resistor unit, as a resistance value corresponding to the set laser irradiating level, when the laser irradiating level is set by a user; and a trigger circuit unit turned on by the user's manipulation to supply a charge voltage of the capacitor to the flash lamp.

In an embodiment of the present disclosure, the voltage increasing unit may include a step-up DC-DC converter for increasing voltage input from the digital variable resistor unit and outputting the increased voltage; and a high voltage booster for boosting voltage input from the step-up DC-DC converter and supplying the boosted voltage to the capacitor.

In an embodiment of the present disclosure, the laser irradiating device may further include a discharge circuit unit turned on under a control of the control unit, thus discharging the charge voltage remaining in the capacitor, if a lock state is set by a safety switch that prevents laser from being irradiated even if the trigger circuit unit is turned on.

In an embodiment of the present disclosure, the trigger circuit unit may be installed in a circuit board that is physically different from a circuit board in which the capacitor, the digital variable resistor unit, and the voltage increasing unit are installed.

In an embodiment of the present disclosure, the capacitor, the digital variable resistor unit, and the voltage increasing unit installed in the physically identical circuit board may be spaced apart from each other by a predetermined insulating distance.

In an embodiment of the present disclosure, the laser irradiating device may further include a screen display unit that reads an output voltage varying depending on a set laser irradiating level and displays the output voltage on a screen.

Advantageous Effects

A laser irradiating device according to the present disclosure is advantageous in that the irradiation intensity of laser may be adjusted by controlling voltage in stages by a user's manipulation, so that a hole having a desired size and depth can be made depending on the purpose of perforation, and a hole having a desired size and depth can be made by adjusting the laser intensity depending on the thickness or nature of skin that varies according to a patient's gender, age, or occupation.

Furthermore, the generation of noise and the leakage of voltage are prevented by physically separating a trigger circuit unit, thus stably adjusting a laser irradiation intensity Furthermore, a capacitor, a digital variable resistor, a voltage increasing unit, and a control unit are installed to be spaced apart from each other by a predetermined insulating distance, thus preventing the generation of noise and the leakage of voltage and thereby stably adjusting a laser irradiation intensity.

DESCRIPTION OF DRAWINGS

FIGS. 1 to 3 are diagrams schematically showing the configuration of a laser irradiating device in accordance with an embodiment of the present disclosure.

FIG. 4 is a diagram illustrating a silicone tip applied to the present disclosure.

FIG. 5 is a diagram illustrating a vacuum glass tube applied to the present disclosure.

MODES OF THE INVENTION

The present disclosure will be described in detail with reference to particular embodiments shown in the accompanying drawings. These embodiments are described in detail so that those skilled in the art can sufficiently implement the present disclosure. It should be understood that various embodiments of the present disclosure are different from each other, but need not be mutually exclusive. For example, specific shapes, structures, and characteristics described herein may be implemented in various ways without departing from the spirit and scope of the present disclosure. Furthermore, it should be understood that the position or arrangement of individual components disclosed in each embodiment may be changed without departing from the spirit and scope of the present disclosure. Therefore, the following detailed description is not intended to be taken in a limiting sense, and the scope of the present disclosure is limited only by claims and equivalence thereof. Like reference numerals denote like components throughout the drawings.

Hereinafter, the preferred embodiments of the present disclosure will be described in detail with reference to the accompanying drawings.

FIGS. 1 to 3 are diagrams schematically showing the configuration of a laser irradiating device in accordance with an embodiment of the present disclosure.

Referring to FIG. 1, a reflector 10 has a receiving space formed therein.

A flash lamp 20 is inserted into the receiving space of the reflector 10 to be spaced apart from a laser rod 30 by a predetermined distance.

The flash lamp 20 generates light to supply energy to the laser rod 30.

The laser rod 30 is inserted into the receiving space of the reflector 10 to induce and focus light emitted by the flash lamp 20.

In other words, the laser rod 30 resonates light incident from the flash lamp 20 to emit the laser beam having high energy.

As a method of oscillating laser, a pulse-type method is used and employs a principle in which the vibration period of a light wave is multiplied by an integer using a medium in the form of resonance to generate a standing wave, thus leading to a rapid increase in induced emission and thereby emitting laser light having the wavelength of 2.94 μm.

The laser rod 30 may be implemented by an Er:YAG crystal.

A focusing lens 40 focuses laser irradiated in a predetermined direction from the laser rod 30 on an accurate focus on the skin from which blood is to be taken.

A total reflection mirror 50 is mounted on a rear surface of the laser rod 30 to totally reflect light focused by the laser rod 30 in a direction where laser is irradiated.

A partial reflection mirror 60 is installed in the direction where the laser is irradiated, i.e. a front surface of the laser rod 30, so that some of the light focused by the laser rod 30 is reflected and the remaining light is emitted.

A skin recognition sensor 70 recognizes the contact of skin such as a finger.

The above-described skin recognition sensor 70 may be implemented as a current sensor that senses a skin contact by sensing a current flowing through a human body, a temperature sensor that senses a skin contact by sensing the temperature of the skin, etc.

The silicone tip 80 covers the finger when blood is taken. If laser is irradiated with the silicone tip 80 covering the finger, the taken blood is accumulated in the tip, thus making it easy to collect the blood.

Such a silicone tip 80 is made of a soft silicone material having elasticity. Thus, if the silicone tip covers the finger, it serves to gather blood while compressing the finger.

Referring to FIGS. 2 and 3, a capacitor 110 stores (charges) voltage that is to be supplied to the flash lamp 20 for a predetermined time.

In an embodiment of the present disclosure, a different voltage for each laser irradiating level is stored in the capacitor 110. This will be described below in detail.

A digital variable resistor unit 120 outputs different voltages according to a resistance value that is set under the control of a control unit 150.

A step-up DC-DC converter 130 boosts voltage that is input from the digital variable resistor unit 120, and then outputs the boosted voltage.

A high voltage booster 140 boosts voltage that is input from the step-up DC-DC converter 130, and then supplies the boosted voltage to the capacitor 110.

As described above, the step-up DC-DC converter 130 and the high voltage booster 140 boost voltage that is input from the digital variable resistor unit 120, and then supply the boosted voltage to the capacitor 110. The voltage that is input from the digital variable resistor unit 120 into the step-up DC-DC converter 130 is changed for each laser irradiating level, so that the output voltage supplied from the high voltage booster 140 to the capacitor 110 is also changed.

The control unit 150 stores a resistance value corresponding to each laser irradiating level. If the laser irradiating level is set by a user, the control unit sets the resistance value of the digital variable resistor unit 120 with the resistance value corresponding to the laser irradiating level that is set by the user.

In an embodiment of the present disclosure, the laser irradiating level may be a total of ten levels including a first level to a tenth level, for example. As the resistance value for each level, the first level may be set to be 20Ω, a second level may be set to be 50Ω, a third level may be set to be 80Ω, a fourth level may be set to be 120Ω, and a fifth level may be set to be 150Ω. According to the resistance value for each level, the digital variable resistor unit 120 outputs voltage, for example, 0.8V (first level), 1.3V (second level), 2V (third level), 2.6V (fourth level), 3.2V (fifth level), etc.

A trigger circuit unit 160 is turned on by a user's manipulation, so that the charge voltage of the capacitor 110 is supplied to the flash lamp 20.

Preferably, the above-described trigger circuit unit 160 is installed in a circuit board that is physically different from a circuit board in which the capacitor 110, the digital variable resistor unit 120, the step-up DC-DC converter 130, the high voltage booster 140, the control unit 150, and the like are installed.

For example, as shown in FIG. 2, the trigger circuit unit 160 may be disposed in a separate circuit board located on the lower end of the reflector 10.

As such, the trigger circuit unit 160 may be installed in the separate circuit board to be insulated from the capacitor 110, the digital variable resistor unit 120, the step-up DC-DC converter 130, the high voltage booster 140, and the control unit 150, thus preventing the leakage of voltage or the generation of noise.

A discharge circuit unit 170 is turned on under the control of the control unit 150, thus discharging the charge voltage remaining in the capacitor 110, if a lock state is set by a safety switch (not shown) that prevents laser from being irradiated even if the trigger circuit unit 160 is turned on.

A screen display unit 180 reads output voltage varying according to the laser irradiating level from the high voltage booster 140 and then displays the output voltage on a screen.

The above-described capacitor 110, digital variable resistor unit 120, step-up DC-DC converter 130, high voltage booster 140, and discharge circuit unit 170 are physically installed in the same circuit board. Preferably, as shown in FIG. 3, these components are separately installed in respective areas to be spaced apart from each other by a predetermined insulating distance.

As such, if the capacitor 110, the digital variable resistor unit 120, the step-up DC-DC converter 130, the high voltage booster 140, and the discharge circuit unit 170 are installed to be spaced apart from each other by a predetermined insulating distance, it is possible to prevent the leakage of voltage or the generation of noise.

Meanwhile, a capacitor comparison unit 190 checks the type of the capacitor 110.

Hereinafter, the operation of the laser irradiating device in accordance with an embodiment of the present disclosure will be described with reference to FIGS. 1 to 5.

First, if a power switch (not shown) is turned on, the control unit 150 checks the laser irradiating level that is set by a user, and thereafter sets the resistance value of the digital variable resistor unit 120 with a resistance value corresponding to the checked laser irradiating level.

For example, assuming that the laser irradiating level is set to be the third level by the user and the resistance value corresponding to the third level is 80Ω, the control unit 150 sets the resistance value of the digital variable resistor unit 120 to be 80Ω. If the laser irradiating level is changed from the third level to the fifth level by the user's manipulation, the resistance value of the digital variable resistor unit 120 is changed from 80Ω to 150Ω.

As described above, if the control unit 150 sets the resistance value of the digital variable resistor unit 120 according to the laser irradiating level that is set, the digital variable resistor unit 120 outputs voltage corresponding to the set resistance value.

For example, when the resistance value of the digital variable resistor unit 120 is set to be 80Ω under the control of the control unit 150, the voltage of 2V is output. When the resistance value thereof is set to be 150Ω, the voltage of 3.2V is output.

As such, the voltage that is output from the digital variable resistor unit 120 is input into the step-up DC-DC converter 130. The step-up DC-DC converter 130 primarily boosts the voltage that is input from the digital variable resistor unit 120, and then outputs the boosted voltage.

The high voltage booster 140 into which voltage primarily boosted and then output in the step-up DC-DC converter 130 is input secondarily boosts voltage that is input from the step-up DC-DC converter 130 to high voltage and then supplies the high voltage to the capacitor 110.

As described above, the resistance value of the digital variable resistor unit 120 is set to a different value for each laser irradiating level, and voltage output from the digital variable resistor unit 120 is changed for each laser irradiating level depending on a differently set resistance value.

Thereby, voltage that is boosted by the step-up DC-DC converter 130 and the high voltage booster 140 and is supplied to the capacitor 110 is also changed for each laser irradiating level.

The capacitor 110 stores voltage that is input from the high voltage booster 140 for a predetermined time (e.g. 250 µS), and then applies the charged voltage to the flash lamp 20 if a trigger signal is generated. Here, only when the safety switch is unlocked even if the user manipulates the trigger switch, the trigger signal is generated. When the safety switch is set in a lock state, the trigger signal is not generated.

The flash lamp 20 receiving the voltage from the capacitor 110 emits light, and light emitted from the flash lamp 20 is focused on the laser rod 30 to shoot laser.

As described above, since the voltage charged to the capacitor 110 is changed for each laser irradiating level, the voltage applied to the flash lamp 20 is also changed. As the voltage applied to the flash lamp 20 is changed, the intensity of light emitted from the flash lamp 20 is also changed. As a result, the laser irradiation intensity from the laser rod 30 is changed.

As described above, in an embodiment of the present disclosure, as the laser irradiation intensity may be adjusted for each level, a hole having a desired size and depth may be made depending on the purpose of perforation. By adjusting the laser intensity depending on the thickness or nature of the skin, which varies depending on the gender, age, or occupation of a patient, a hole having a desired size and depth may be made.

Meanwhile, after the laser irradiation intensity is adjusted for each level and laser is irradiated, the safety switch is locked such that laser is not irradiated by mistake. If the safety switch is in the lock state, the control unit 150 turns on the discharge circuit unit 170 to discharge the charge voltage remaining in the capacitor 110, thus securing the safety of the laser irradiating device.

Furthermore, in an embodiment of the present disclosure, the trigger circuit unit 160 may be disposed on a separate circuit board located on the lower end of the reflector 10, as shown in FIG. 2, thus preventing the generation of noise and the leakage of voltage and thereby stably adjusting the laser irradiation intensity.

Furthermore, in an embodiment of the present disclosure, as shown in FIG. 3, after the capacitor 110, the digital variable resistor unit 120, the step-up DC-DC converter 130, the high voltage booster 140, and the discharge circuit unit 170 are separately installed in respective areas, they are spaced apart from each other by a predetermined insulating distance, thus preventing the generation of noise and the leakage of voltage and thereby stably adjusting the laser irradiation intensity.

Meanwhile, a user pus the skin of the finger or the like on a front end of the laser irradiating device so as to take blood. In this case, the laser may be irradiated after the silicone tip 80 covers the finger, as shown in FIG. 4.

As such, if the laser is irradiated with the silicone tip 80 covering the finger, the taken blood may be accumulated in the tip, thus making it easier to collect the blood.

The taken blood may be collected through a vacuum glass tube shown in FIG. 5.

The vacuum glass tube has a vacuum state therein, and a tube plugged into the glass tube is also closed by a rubber stopper.

When the taken blood is collected, the rubber stopper closing the tube is removed and then an end of the tube comes into contact with the taken blood. If a cap of the glass tube is slowly turned in one direction, the taken blood is sucked into the glass tube through the tube.

If the taken blood is collected, the tube is closed again using the rubber stopper and the cap of the glass tube is also turned in an opposite direction to be closed.

Although the foregoing description is merely for illustrative purposes, it is apparent to those skilled in the art that the present disclosure may be changed and modified in various ways without departing from the scope of the present disclosure, which is described in the following claims.

The invention claimed is:

1. A laser irradiating device comprising:
    a reflector having a receiving space formed therein;
    a flash lamp inserted and mounted in the reflector to generate light;
    a laser rod for resonating light incident from the flash lamp to emit a laser;
    a capacitor for storing, for a predetermined time, voltage to be supplied to the flash lamp;
    a digital variable resistor unit for outputting different voltages according to set resistance values;
    a voltage increasing unit for increasing voltage input from the digital variable resistor unit and supplying the increased voltage to the capacitor;
    a control unit storing resistance values corresponding to laser irradiating levels and setting a resistance value of the digital variable resistor unit, as a resistance value corresponding to the set laser irradiating level, when the laser irradiating level is set by a user; and
    a trigger circuit unit turned on by the user's manipulation to supply a charge voltage of the capacitor to the flash lamp.

2. The laser irradiating device of claim 1, wherein the voltage increasing unit comprises:
    a step-up DC-DC converter for increasing voltage input from the digital variable resistor unit and outputting the increased voltage; and
    a high voltage booster for boosting voltage input from the step-up DC-DC converter and supplying the boosted voltage to the capacitor.

3. The laser irradiating device of claim 1, further comprising:
    a discharge circuit unit turned on under a control of the control unit, thus discharging the charge voltage remaining in the capacitor, if a lock state is set by a safety switch that prevents laser from being irradiated even if the trigger circuit unit is turned on.

4. The laser irradiating device of claim 1, wherein the trigger circuit unit is installed in a circuit board that is physically different from a circuit board in which the capacitor, the digital variable resistor unit, and the voltage increasing unit are installed.

5. The laser irradiating device of claim 1, wherein the capacitor, the digital variable resistor unit, and the voltage increasing unit installed in the physically identical circuit board are spaced apart from each other by a predetermined insulating distance.

6. The laser irradiating device of claim 1, further comprising:
    a screen display unit reading output voltage that varies depending on a laser irradiating level to display the output voltage on a screen.

* * * * *